United States Patent
Balaban

(10) Patent No.: US 6,994,878 B2
(45) Date of Patent: *Feb. 7, 2006

(54) METHOD AND APPARATUS FOR CONTINUOUS FLOW REDUCTION OF MICROBIAL AND/OR ENZYMATIC ACTIVITY IN A LIQUID BEER PRODUCT USING CARBON DIOXIDE

(75) Inventor: Murat O. Balaban, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/798,837

(22) Filed: Mar. 12, 2004

(65) Prior Publication Data

US 2004/0234661 A1    Nov. 25, 2004

Related U.S. Application Data

(60) Continuation-in-part of application No. 10/662,883, filed on Sep. 16, 2003, now abandoned, which is a division of application No. 10/136,378, filed on May 2, 2000, now Pat. No. 6,723,365, which is a continuation of application No. 09/613,714, filed on Jul. 11, 2000, now abandoned, which is a continuation-in-part of application No. 09/314,945, filed on May 20, 1999, now abandoned.

(60) Provisional application No. 60/095,967, filed on Aug. 10, 1998.

(51) Int. Cl.
*A23L 3/00* (2006.01)

(52) U.S. Cl. ........... 426/330.4; 426/320; 426/532; 426/592; 426/521

(58) Field of Classification Search ............... 426/521, 426/592, 330, 330.4, 532, 312, 320; 99/323.1, 99/323.2; 422/255
See application file for complete search history.

(56) References Cited

U.S. PATENT DOCUMENTS

| | | | |
|---|---|---|---|
| 2,356,498 | A | 8/1944 | Bargeboer |
| 2,569,217 | A | 9/1951 | Bagdigian |
| 2,713,232 | A | 7/1955 | Peterson |
| 2,838,403 | A | 6/1958 | Notter |
| 2,967,777 | A | 1/1961 | Grindrod |
| 3,442,660 | A | 5/1969 | Shank |
| 3,477,856 | A | 11/1969 | Schultz |
| 3,597,235 | A | 8/1971 | Kramer |
| 4,048,342 | A | 9/1977 | Haas et al. |
| 4,049,835 | A | 9/1977 | Haas et al. |
| 4,310,560 | A | 1/1982 | Doster et al. |
| 4,664,922 | A | 5/1987 | Leon et al. |
| 4,804,552 | A | 2/1989 | Ahmed et al. |
| 4,919,960 | A | 4/1990 | Ahmed et al. |
| 5,232,726 | A | 8/1993 | Clark et al. |
| 5,393,547 | A | 2/1995 | Balaban et al. |
| 5,520,943 | A | 5/1996 | Osajima et al. |
| 5,667,835 | A | 9/1997 | Osajima et al. |
| 5,704,276 | A | 1/1998 | Osajimma et al. |
| 5,869,123 | A | 2/1999 | Osajima et al. |

FOREIGN PATENT DOCUMENTS

| | | |
|---|---|---|
| CA | 2280240 | 2/2000 |
| EP | 015184 | 12/1981 |
| EP | 812544 | 12/1997 |
| GB | 332641 | 7/1930 |
| JP | 3027268 | 2/1991 |
| WO | WO 89/02221 | 3/1989 |

OTHER PUBLICATIONS

Kamihira, M. et al., "Sterilization of microorganisms with supercritical carbon dioxide", Agricultural and Biological Chemistry, vol. 51, No. 2, pp. 407-412 (1987) (abstract).

Arreola, A.G. et al., "Supercritical carbon dioxide effects on some quality attributes of single strength orange juice", J. of Food Science, vol. 56, No. 4, pp. 1030-1033 (1991) (abstract).

Ishikawa, H. et al., "Sterilization of microorganisms by the supercritical carbon dioxide micro-bubble method", Bioscience, Biotechnology and Biochemistry, vol. 59, No. 10, pp. 1949-1950 (1995).
Yun, H. et al., "Effect of a combined treatment of high hydrostatic pressure and carbonation on the quality characteristics of Valencia orange juice", Korean J. of Food Science and Technology, 29(5), pp. 974-981 (1997) (abstract).
Balaban, M.O. et al., "Enzyme Inactivation by Pressurized Carbon Dioxide", Science for the Food Industry of the 21$^{st}$ Century (Yalpani, M. ed., ATL Press), pp. 239-251 (1993).
Arreola, A.G. et al., "Effect of Supercritical Carbon Dioxide on Microbial Populations in Single Strength Orange Juice", J. of Food Quality, 14, pp. 275-284 (1991).
CA, Tan et al., vol. 97, p. 180442e (1982).
CA, Pichard et al., vol. 102, p. 91875c (1985).
CA, Crouzet et al., vol. 105, p. 77759y (1986).
CA, Kramer et al., vol. 93, p. 148368s (1980).
CA, Taniguchi et al., vol. 105, p. 113696m (1986).
Abstract, No. 381, "Nonthermal inactivation of pectinesterase from orange juice", 1987, Institute of Food Technologists Annual Meeting (Jun. 16-19, 1987).
Owusu-Yaw et al., "Low pH Inactivation of Pectinesterase in Single Strength Orange Juice", J. Food Sci., vol. 53, pp. 504-507 (1988).
Fife et al., "The Effect of Carbon Dioxide Upon the pH and Certain Nitrogen Fractions of the Sugar-Beet Plant", pp. 643-655 (1935).
Van Slyke et al., "Effect of Treating Milk with Carbon Dioxide Gas Under", New York Agricultural Experiment Station, Bulletin No. 292, pp 371-384 (Aug. 1907).
King et al., "Preservation of raw milk by the addition of carbon dioxide", Journal of Diary Research, 49, pp. 439-447 (1982).
Mabbit, "Preservation of refrigerated milk", National Institute for Research in Dairying, Shinfield, Reading, England, Kieler Milchwirtschaftliche Forschungsberichte 34(1) pp. 28-31 (1982).
King et al., "The Use of Carbon Dioxide for the Preservation of Milk", Society for Applied Bacteriology, Series #22, pp. 35-43 (1987).
Rowe, "Effect of carbon dioxide on growth and extracellular enzyme production by *Pseudomonas fluorescens* B52", International Journal of Food Microbiology, 6, pp. 51-56 (1988).
Rowe, "Carbon dioxide to prolong the safe storage of raw milk", Milk Industry 91(7), pp. 17-19 (1989).
Rowe, "Effect of carbon dioxide on growth and extracellular enzyme production by Pseudomonas fluorescens B52", International Journal of Food Microbiology, 6, pp. 51-56 (1988).

Maniar et al., "Modified Atmosphere Packaging to Maintain Direct-Set Cottage Cheese Quality", Journal of Food Science, vol. 59, No. 6, pp. 1305-1308 (1994).
Hotchkiss et al., "Extending shelf-life of dairy products with dissolved carbon dioxide", European Dairy Magazine, No. 3, pp. 16, 18-19 (1996).
Goraki, "Commitment to Cottage Cheese", Dairy Foods Ingredient Technology Lab Talk, p. 29, Apr. (1996).
M.G. Gänzle, et al., "High Pressure Inactivation of *Lactobacillus plantarum* in a Model Beer System", Journal of Food Science, vol. 66, No. 8, 2001, pp 1174-1181.
M. Castellari et al., "High Hydrostatic Pressure Treatments for Beer Stabilization", Journal of Food Science, vol. 65, No. 6, 2000, pp. 974-977.

*Primary Examiner*—Drew Becker
(74) *Attorney, Agent, or Firm*—Miles & Stockbridge P.C.; Dennis P. Clarke

(57) ABSTRACT

A continuous method for reducing one or more of microorganisms or enzymes in a liquid beer or wine product, the method comprising the steps of:
  a) forming a pressurized mixture by
    i) combining a pressurized flow of the liquid beer or wine product with a flow of pressurized liquefied carbon dioxide to create a pressurized mixture in a flow state, the carbon dioxide at a pressure sufficient to maintain it in a liquid state and at a temperature which does not freeze the liquid beer or wine product; or
    ii) forming a mixture of the liquid beer or wine product 15 with liquid or gaseous carbon dioxide, wherein the carbon dioxide if in the liquid state is at a pressure sufficient to maintain it in a liquid state and at a temperature which does not freeze the liquid beer or wine product, and then pressurizing the mixture;
  b) flowing the pressurized mixture through a reaction zone for a sufficient time to reduce at least one of the microorganisms and the enzymes in the liquid mixture;
  c) feeding the pressurized mixture from the reaction zone through one or more expansion stages wherein the pressure of the mixture flow is decreased to vaporize the carbon dioxide in the mixture; and
  d) applying heat in at least one of the expansion stages to the mixture if necessary, to the extent necessary, to prevent cooling of the carbon dioxide from causing freezing of the liquid product.

10 Claims, 2 Drawing Sheets

METHOD AND APPARATUS FOR CONTINUOUS FLOW REDUCTION OF MICROBIAL AND/OR ENZYMATIC ACTIVITY IN A LIQUID BEER PRODUCT USING CARBON DIOXIDE

RELATED APPLICATIONS

This application is a continuation-in-part of U.S. patent application Ser. No. 10/662,883, filed Sep. 16, 2003 (abandoned), which is a division of U.S. patent application Ser. No. 10/136,378, filed May 2, 2002 (U.S. Pat. No. 6,723,365), which is a continuation of patent application Ser. No. 09/613,714, filed Jul. 11, 2000 (abandoned), which is a continuation-in-part of patent application Ser. No. 09/314,945, filed May 20, 1999 (abandoned), and claims priority from U.S. provisional application Ser. No. 60/095,967 filed Aug. 10, 1998, the entire contents and disclosures of which are incorporated herein by reference.

FIELD OF THE INVENTION

This invention relates to a method and apparatus for the processing of liquid beer products to reduce microbial and/or enzymatic activity therein and, more particularly, to the use of carbon dioxide to achieve reductions of microbial and/or enzymatic activity.

BACKGROUND OF THE INVENTION

There are many methods for improving the shelf life of liquid products such as orange juice, apple juice, milk, latex paints, peanut butter, soup, etc. Commercially, thermal methods such as pasteurization are the predominant methods used to improve the shelf life of liquid foods. Ultra-high pressure treatment is also used for liquid foods, but less frequently.

In ultra-high pressure treatment facilities, fluids containing microbial contamination are pressurized hydrostatically to kill the majority of the bacteria. In such systems, pressures are created which equal or exceed 30,000 psia and commonly range from 60,000 to 120,000 psia. Such hydrostatic treatment, however, has potential safety risks because of the very high pressures, is batch rather than continuous, and is expensive due to the high capital costs of the required equipment.

Other methods for shelf-life extension of liquids include ionizing irradiation, ultra-violet exposure and application of microwaves. These treatments are expensive and not widely used commercially at present.

High pressure homogenization has also been used to increase the shelf life of orange juice and other single-strength citrus juices as described in U.S. Pat. No. 5,232,726 to Clark et al. It is disclosed therein that a citrus juice being processed is subjected to a high pressure of about 15,000 psia, with the result being a significant reduction in microbial, but not enzymatic, activity in the juice.

Carbon dioxide has been used to inactivate enzymes in food and reduce microbial populations in fruit juices as described in U.S. Pat. No. 5,393,547 to Balaban et al. Balaban et al. describe a method for inactivating enzymes in liquid food products wherein the food is exposed to pressurized carbon dioxide which, in turn, produces a carbonic acid solution with a pH that is sufficiently low to irreversibly inactivate enzymes in the liquid food. The Balaban et al. method is indicated as being applicable to either batch mode or continuous flow mode processing of food. Balaban et al. further indicate that supercritical carbon dioxide is introduced at a rate sufficient to allow enough thereof to dissolve in the food to inactivate the enzymes. After enzymatic inactivation, the food flows to a section where pressure is reduced and the released carbon dioxide may be recycled for repeat usage.

U.S. Pat. No. 5,704,276 to Osajima et al. describes a method for continuous deactivation of enzymes in liquid foodstuffs, using a supercritical form of carbon dioxide. Osajima et al. indicate that the density of the supercritical fluid is less than that of the liquid food and that the supercritical carbon dioxide is injected continuously into the liquid food and is separated therefrom in a later stage of the process. Osajima et al. also indicate that their process deodorizes the liquid food and removes volatile components.

Arreola et al. in "Effect of Supercritical Carbon Dioxide on Microbial Populations in Single Strength Orange Juice", Journal of Food Quality, Volume 14 (1991), pp. 275–284, describe the effect of supercritical carbon dioxide on microbial populations in orange juice. Using a batch process, Arreola et al. concluded that high pressure carbon dioxide treatment resulted in microbial reduction in single strength orange juice, even at low temperatures. Further, they conclude that a combination of high pressure, and shear forces to which the orange juice is subjected during depressurization and lower pH due to temporary formation of carbonic acid may have further inhibitory effects on the normal flora within orange juice. During the processing described in this paper, the minimum temperature utilized was 35° C.

Although pasteurization has been used in the wine and brewing industry for many years, having been developed around 1865 by Louis Pasteur, significant difficulties are encountered in pasteurizing brewed alcoholic liquids such as beer and wine. Pasteurization is the reduction of microorganisms by heating to a limited temperature and holding at that temperature such that there will be minimum effect on physical stability and flavor and a maximum extension of biological stability, thereby increasing shelf life.

The organisms which cause the most difficulty in the beer and wine brewing industry today are *lactobacillus, pedioococcus* and wild yeast. These are not pathogenic organisms but can cause turbidity and poor taste in beer and wine. In order to insure complete pasteurization, the temperature of beer at the so-called "cold spot" which is ¼ from the bottom of the center of the can or bottle must reach at least 140° F. for a period of time sufficient to produce a specified number of pasteurization units (P.U.). It also is desired to pasteurize at the lowest possible peak cold spot temperature (above 140° F.) to avoid overheating the rest of the package contents, because the temperature of the package gets higher as one goes from the cold spot towards the surface of the package.

The P.U. is a measure of accumulated lethality. One P.U. for beer is one minute at 140° F. Lethality (P.U. per minute) is a rate term which is exponential with temperature. Lethality begins to become significant only when the beer temperature is 132° F. to 135° F. and is most significant at 139° F. and above, although P.U. accumulation begins at 120° F.

Over the years different minimum P.U. have been stated as the requirement for pasteurizing beer, but it is clear that at least 5.6 P.U. are required and if numerous organisms are present, a standard of 8 P.U. has been set forth. Some breweries require a minimum of 10 P.U. as their standard. It has been determined that *Lactobacillus Brevis* is the most heat resistant bacteria normally occurring in beer. It is this organism that brewery pasteurization of beer requires 140° F. as the minimum standard temperature for pasteurization.

The various organisms present in beer are not pathogenic and dangerous to humans, but affect the taste and appearance of the beer if allowed to grow. Draft beer generally is not pasteurized because it is kept refrigerated and is usually consumed in a short time. However, high quality canned and bottled beer traditionally is pasteurized for long shelf life, and conventional type pastuerizers are shown in Herold U.S. Pat. No. 2,282,187 issued May 5, 1942 and Wehmiller U.S. Pat. No. 2,658,608 dated Nov. 10, 1953.

In these type pasteurizers, water is sprayed onto the tops of the closely packed packages which are moved through a tunnel which is divided into a series of preheat zones, a series of heating zones, a holding zone, and a series of cooling zones. The temperature of the beer in the containers is progressively raised to the desired level before being passed through the cooling zones where it reaches the desired beer out temperature (BOT). The water running off the packages is collected in reservoirs, heated or cooled, and recycled to the sprays of spray pans. These types of tunnel pasteurizers are available in single and double deck configurations. The spray nozzles on the lower decks traditionally are difficult to maintain free from blockage, so the single deck conveyor has been the generally accepted norm in the brewing industry in the United States.

If pasteurization causes the temperature of the beer to reach too high a level, certain tastes called "pasteurization tastes" can occur in the beer. These are undesirable and have been defined as "bready", "biscuity", "burnt-type tastes", "papery" or "cardboardy". Also, insufficient pasteurization can result in turbidity of the beer or sedimentation due to microbial growth.

A similar process as described in the preceding paragraph is disclosed in EP-A2-0 430 907, wherein liquid contained in containers, such as beer in bottles or cans, is passed through a tunnel pasteurizer at constant speed, and pasteurized therein through heating up the containers and cooling them down again by means of spraying with water. During a normal, continuous feed-through of containers, the liquid in the containers is first heated up in the pre-heating area to near the pasteurization temperature and is subsequently heated in the pre-pasteurization zone to the pasteurization temperature by spraying the containers with water received in that zone, which is heated up again to a temperature higher than the pasteurization temperature. In the pasteurization zone, the containers are sprayed with water recirculated in that zone, which water is maintained at a suitable pasteurization temperature. After having passed through the pasteurization zone, the containers are cooled again in the cooling area, the containers in the first cooling zone being sprayed with water received in the last pre-heating zone. The water received in the first cooling zone, which was used as spray water and has hence withdrawn heat from the containers, is in turn fed back again to the last pre-heating zone.

This process has as a drawback that in particular starting up or, after a failure, restarting the pasteurization, requires much energy, while, moreover, during a failure in the feed-through of containers through the pasteurizer, much energy is lost. In addition, during the pasteurization, the normal, continuous feed-through of the containers requires much energy for pumping round the spray water and bringing it to a temperature and maintaining it at that temperature.

Thus, for the sale and distribution of beer (and wines) to distant locales following brewing and bottling, it is important that, after packaging, thermal destruction of microorganisms, e.g. by pasteurization, is performed in the packages, in order to ensure sterility and to prevent product damage, such as flavor impairment, by the action of beer-spoilage microorganisms. However, this approach has the considerable disadvantage that the yeast introduced for the purpose of secondary fermentation can no longer develop its activity and thus the oxygen in the container is no longer metabolized. In addition, the tendency of the oxygen to react with the beer present in the container is activated, or enlivened, at higher temperatures and, thus, by the temperature increase in the pasteurization, which leads to an accelerated "aging process" of the beer. Owing to the interaction with the oxygen, the flavor quality of the beer therefore deteriorates with time, which is further reinforced by temperature effects and movements.

Although the addition of active compounds, such as ascorbic acid or vitamin C, which is sometimes practiced in the case of other beverages can restrict these problems, in some countries it is not used for beer in view of purity laws which exist in some countries, such as Germany.

It is an object of this invention to provide an improved method and apparatus for reducing microbial and/or enzymatic activity in liquid beer and wine products.

It is a further object of this invention to provide a method and apparatus for reducing microbial and/or enzymatic activity in liquid beer and wine products using pressurized carbon dioxide, wherein the processing temperature to which the liquid is subjected does not deleteriously affect the liquid products.

It is yet another object of this invention to provide a continuous flow method and apparatus for reducing microbial and/or enzymatic activity in liquid beer and wine products using pressurized carbon dioxide.

SUMMARY OF THE INVENTION

A continuous method using a pressurized flow of carbon dioxide is described for the reduction of microorganisms present in liquid beer and wine products and/or the inactivation of one or more enzymes in a pressurized flow of the liquid products. In one embodiment, the pressure in the flow regions is maintained at a level which is sufficient to keep the carbon dioxide in dense phase (e.g., liquid or supercritical), but at a temperature which does not freeze the liquid product. In another embodiment, gaseous carbon dioxide is injected directly into the liquid product, forming a mixture which is thereafter pressurized.

The pressurized mixture of the carbon dioxide and liquid flows through a reaction zone for a sufficient time to reduce harmful microorganisms and inactivate enzymes and then enters one or a plurality of expansion stages wherein the pressure of the mixture flow is decreased sufficiently to allow the separation of carbon dioxide from the liquid product. Heat is applied if necessary, to the extent necessary, in at least some of the expansion stages to prevent a cooling of the mixture flow to the freezing point of the liquid product. If heat is applied, the temperature should preferably be controlled so that the liquid does not exceed a temperature at which deleterious effects are experienced. (Freezing and excessive high temperature can have negative effects on the product quality. Temperatures over 40° C. begin to degrade the product.)

The present invention is contemplated for use with any fluid that may be transported through a conduit, in particular, beverage products such as wines and beers.

DETAILED DESCRIPTION OF THE INVENTION

Figure 1:
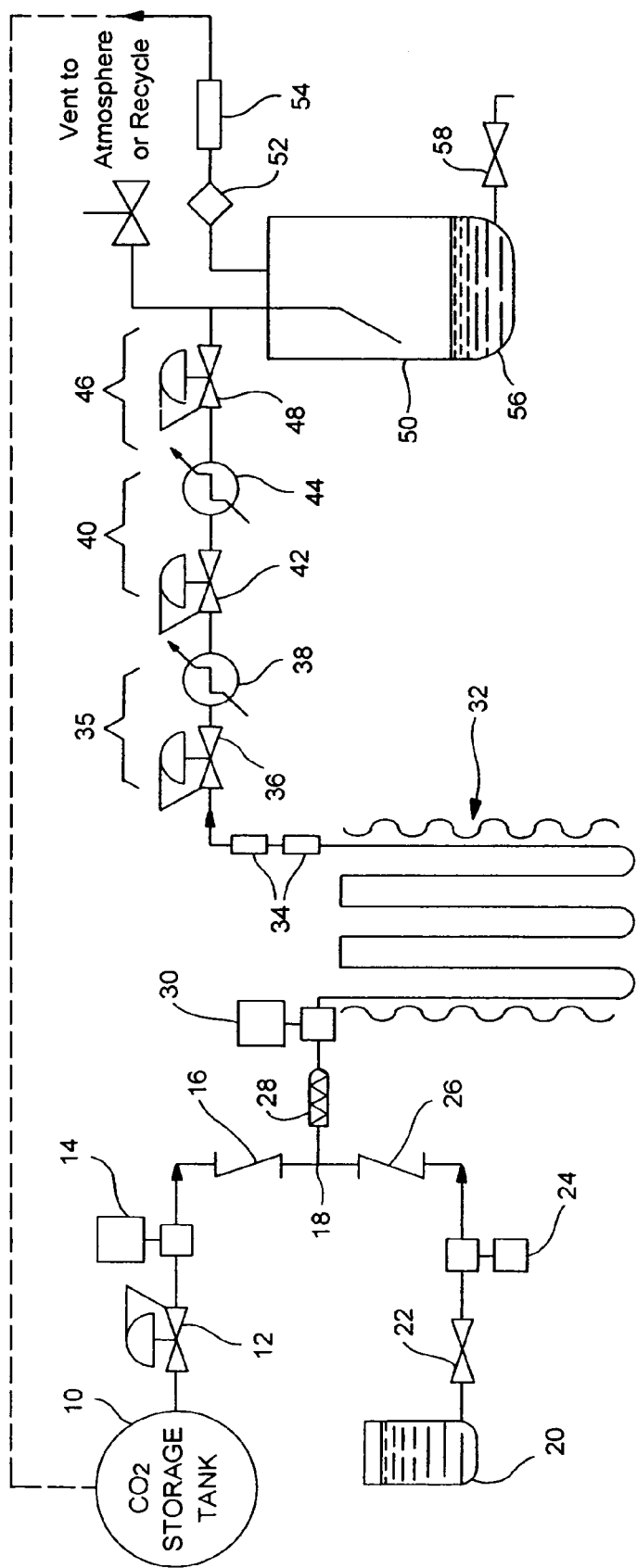
FIG. 1 is a schematic flow diagram of apparatus which performs one embodiment of the invention.

Referring to FIG. 1, pressurized carbon dioxide is fed from carbon dioxide supply 10 through optional pressure regulator 12 to a pump 14 which increases the pressure of the carbon dioxide flow and then feeds it through a check valve 16 to a juncture 18. The carbon dioxide is pressurized at pump 14 to prevent any boiling of the dense phase carbon dioxide during later stages of the process. In similar fashion, liquid product is fed from a 30 liquid product feed tank 20 through a valve 22 to a pump 24. Pump 24 raises the feed pressure of the liquid product to the same level as that of the dense phase carbon dioxide exiting from pump 14. The pressurized liquid product feed passes through check valve 26 to juncture 18 where it combines with the pressurized flow of carbon dioxide. The mixture of the liquid product and carbon dioxide then passes to an inline mixer 28 (optional) which essentially comprises a heavily baffled conduit that thoroughly mixes the carbon dioxide and liquid product streams. Of course, other mixers may be employed which achieve a desired level of liquid product/carbon dioxide mixing. The liquid mixture exits from in-line mixer 28 and is further pressurized by the action of pump 30 to a process pressure.

Depending upon the specific liquid product feed, the process pressure will vary accordingly. It is preferred that the process pressure be within the range of 300 psia to 20,000 psia. If beer is being processed, a preferred range of pressure is about 1500 psia to about 7500 psia.

Figure 2:
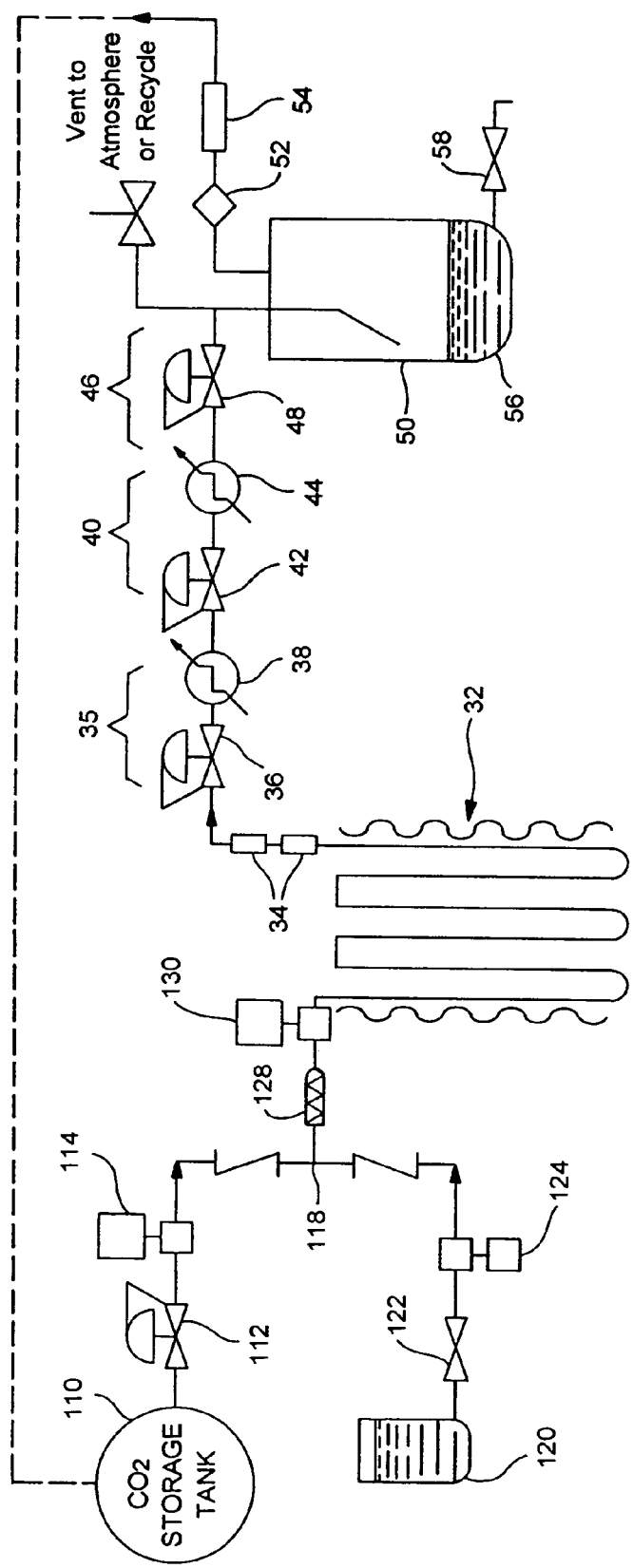
FIG. 2 is a schematic flow diagram of apparatus which performs another embodiment of the invention.

Referring to FIG. 2, carbon dioxide is fed from source 110 through optional pressure regulator 112. Pump 114 can pressurize the carbon dioxide to dense phase or liquid and convey it to juncture 118, or if the carbon dioxide is gaseous then pump 114 can be omitted and the gas flows under its own pressure to juncture 118. Separately, liquid product is fed from liquid product feed tank 120 through valve 122. Preferably, a pump 124 helps convey the liquid product to juncture 118 but need not pressurize the liquid product.

The liquid product and the carbon dioxide are mixed together, in-line (for instance at juncture 118) or for instance with the aid of optional mixing device 128 (which could be at juncture 118). If the carbon dioxide is liquid, an in-line mixer or equivalent device can be used as described with respect to device 28 in FIG. 1. If the carbon dioxide is gaseous, any device effective to feed the gas into the liquid product can be used, such as a sparger, in-line injector, sidestream injection, ultrasonic transducers, or mixing with dry ice. Injection devices include membranes, sintered metal spargers, flexible diffusers, sidestream ejectors, venturi injectors, and equivalent ("Praso") valves. The gaseous carbon dioxide can be fed into the feed line through which the liquid product passes, or into a holding tank (not shown) located at a point in the feed line between juncture 118 and pump 130. Then the mixture is pressurized at pump 130 to process pressure.

Once the liquid mixture however formed exits from 20 pump or 130, it enters a reaction zone 32 that is of suitable size and length to provide sufficient contact (or residence) time for the carbon dioxide and liquid product to interact in a manner which reduces microorganisms and/or inactivates enzymes including undesirable enzymes present in the liquid product. The selected residence time will depend on the liquid product to be processed and its flowrate, as well as the size and length of the reaction zone. It is preferred that the reaction zone residence time is in the range of about 1.0 to about 15.0 minutes.

For example, for processing beer, at a flowrate of 500 ml/min in a reaction zone having a length of about 260 feet and tubing size of about ¼ inch (0.95 mm) inner diameter (I.D.), the preferred residence time is about 1 to 10 minutes, and more preferably about 5 minutes of residence time. This typically reduces viable yeasts by 7 log cycles.

As the liquid mixture stream exits from reaction zone 32, it enters one or more interaction chambers 34 (optional) wherein high shear forces are applied which enable a rupture of microbial cell walls in the liquid mixture. Such action enables a further reduction of the microbial populations in the liquid mixture. For example, a high shear interaction chamber can be used, one example of which suitable for inclusion in this process is manufactured by the Microfluidics International Corp., Newton, Mass. Homogenizers are also useful for this purpose.

At this stage, the pressurized carbon dioxide/liquid product mixture must be depressurized in such a fashion as to avoid freezing the liquid product (due to the Joule-Thompson cooling effect of the expansion of the carbon dioxide). If the pressure is lowered to ambient in one or two stages, application of supplemental heat may be required. If too much heat is added to the mixture, damage will occur to the liquid product, either in its flavor characteristics or its composition. Also, important volatiles such as flavor components may be carried away. Accordingly, it has been found that substantial care must be taken during the depressurization action to maintain the liquid mixture within two boundaries. The lower boundary is the freezing point of the liquid mixture and the upper boundary point is the maximum temperature to which the liquid product can be subjected, without damage to the product.

In the case of beer, the maximum temperature is about 35° C. and the minimum temperature is about 0° C. Accordingly, when choosing a pressure reduction scheme, a pressure/enthalpy chart for carbon dioxide is followed to determine the optimum pressure and heating temperature needed for plural pressure reduction stages, while keeping (in this example) the beer at a temperature between that which will injure its flavor and its freezing point. It has been determined that at least two stages of depressurization are preferred, but one or multiple stages are possible.

Returning to FIG. 1, while one or more depressurization stages can be used, three are shown.

The first depressurization stage includes a pressure control device 36, such as a back pressure regulator, followed by a heat exchanger 38. Assuming that the liquid product being processed is beer and that the process pressure within reaction zone 32 and (optional) interaction chamber 34 is about 5,000 psig, a first depressurization stage 35 reduces the pressure of the liquid mixture to approximately 500 psig and applies sufficient heat through heat exchanger 38 to maintain the liquid mixture at about 20° C.

A second optional depressurization stage 40 includes a pressure control device 42 and heat exchanger 44 which, in combination, reduce the pressure of the liquid mixture to about 250 psia and maintains its temperature at approximately 30° C. A final stage depressurizer 46 includes only a pressure control device 48 to reduce the pressure of the liquid mixture to the point where the dense phase carbon dioxide will vaporize and may be separated from the liquid products while minimizing loss of important volatile components. In the embodiment shown in the figure, no heat exchanger is required subsequent to pressure control device 48, however, one may be provided, if required, to maintain the liquid mixture within the required temperature range.

As the liquid mixture exits from pressure control device 48, it enters a liquid product/carbon dioxide separator vessel 50 or other collection device at reduced pressure. There, the carbon dioxide vapor separates from the liquid product, is captured and (if desired) is passed through optional filter 52 and/or optional flow meter 54 and is either vented to atmosphere or is passed through a pressurization stage (not shown) for recycling back to carbon dioxide supply 10. The liquid product pool 56 may then be drained through valve 58 for subsequent processing and/or use.

In the case of beer or other carbonated beverages, the last depressurization stage is important. The $CO_2$ pressure is reduced only to the levels acceptable for the desired carbonation of the product. This can be the original level of $CO_2$ present in the beer. In the case of non-carbonated beverages such as most wines, for example, the depressurization stage may comprise complete removal of the $CO_2$.

It is to be understood, that the continuous process method shown in the figure is made practical by the one or more, preferably multiple, depressurization stages which enable the liquid mixture to be maintained within the aforementioned temperature boundaries. As a result, a continuous process for reduction of microbial and/or enzymatic activity is achieved while overcoming the principal problem of the prior art, i.e., batch processing which is an uneconomic and undesired processing procedure in a commercial environment.

If the carbon dioxide gas is to be recycled, it may be passed through a coalescing filter to remove droplets of the processed liquid product. Thereafter, the gas is recondensed, or compressed, to the liquid state by passage through a condensing heat exchanger or compressor. Further, to assure removal of the dissolved carbon dioxide in the processed liquid product, a liquid product/carbon dioxide separator downstream from separator tank 50 may include means for dissolved gas removal. The resultant gas, remaining after processing, may carry additional valuable aromas and/or flavors. To recover or remove such aromas or flavors, a method such as condensation or absorption may be utilized.

It should be understood that the foregoing description is only illustrative of the invention. Various alternatives and modifications can be devised by those skilled in the art without departing from the invention.

What is claimed is:

1. A continuous method for reducing one or more of microorganisms or enzymes in a liquid beer or wine product, said method comprising the steps of:
    a) forming a pressurized mixture by
        i) combining a pressurized flow of said liquid beer or wine product with a flow of pressurized liquefied carbon dioxide to create a pressurized mixture in a flow state, said carbon dioxide at a pressure sufficient to maintain it in a dense phase and at a temperature which does not freeze said liquid beer or wine product; or
        ii) forming a mixture of said liquid beer or wine product with liquid or gaseous carbon dioxide, wherein said carbon dioxide if in the liquid state is at a pressure sufficient to maintain it in a liquid state and at a temperature which does not freeze said liquid beer or wine product, and then pressurizing said mixture;
    b) flowing said pressurized mixture through a reaction zone for a sufficient time to reduce at least one of said microorganisms and said enzymes in said liquid mixture;
    c) feeding said pressurized mixture from said reaction zone through one or more expansion stages wherein the pressure of said mixture flow is decreased to vaporize the carbon dioxide in said mixture; and
    d) applying heat in at least one of said expansion stages to said mixture if necessary, to the extent necessary, to prevent cooling of said carbon dioxide from causing freezing of said liquid product.

2. The continuous method of claim 1, wherein the time in step b) is about 30 seconds to about 15 minutes.

3. The continuous method of claim 1, wherein step d) maintains the temperature of said mixture within a range between the freezing temperature of said liquid beer or wine product and about 35° C.

4. The continuous method claim 1 wherein step b) feeds said pressurized flow of said mixture in said reaction zone at a pressure of about 1000 psia.

5. The continuous method of claim 1, wherein step a) comprises forming a mixture of said liquid beer or wine product with liquid or gaseous carbon dioxide, wherein said carbon dioxide if in the liquid state is at a pressure sufficient to maintain it in a liquid state and at a temperature which does not freeze said liquid product, and then pressurizing said mixture.

6. The continuous method of claim 5, wherein in step d) heat is applied to said mixture in at least one of said expansion stages.

7. The continuous method of claim 6 wherein step d) maintains the temperature of said mixture within a range between the freezing temperature of said liquid product and about 35° C.

8. The continuous method of claim 5 wherein step c) feeds said mixture flow through two or more expansion stages to vaporize said liquefied carbon dioxide.

9. The continuous method of claim 5 wherein step b) feeds said pressurized flow of said mixture in said reaction zone at a pressure within a range of about 1500 psia to about 7500 psia.

10. The continuous method of claim 5 wherein step b) maintains said pressurized flow of said mixture in said reaction zone for a duration of from about 30 seconds to about 15 minutes.

\* \* \* \* \*